(12) United States Patent
Boon

(10) Patent No.: US 10,722,219 B2
(45) Date of Patent: Jul. 28, 2020

(54) SYSTEM AND METHOD FOR QUANTITATIVE MUSCLE ULTRASOUND FOR DIAGNOSIS OF NEUROMUSCULAR DISEASE

(71) Applicant: MAYO FOUNDATION FOR MEDICAL EDUCATION AND RESEARCH, Rochester, MN (US)

(72) Inventor: Andrea J. Boon, Byron, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 586 days.

(21) Appl. No.: 15/320,471

(22) PCT Filed: Jun. 24, 2015

(86) PCT No.: PCT/US2015/037444
§ 371 (c)(1),
(2) Date: Dec. 20, 2016

(87) PCT Pub. No.: WO2015/200494
PCT Pub. Date: Dec. 30, 2015

(65) Prior Publication Data
US 2017/0196541 A1 Jul. 13, 2017

Related U.S. Application Data

(60) Provisional application No. 62/016,945, filed on Jun. 25, 2014.

(51) Int. Cl.
A61B 8/00 (2006.01)
A61B 8/08 (2006.01)
A61B 8/14 (2006.01)

(52) U.S. Cl.
CPC .............. *A61B 8/5215* (2013.01); *A61B 8/08* (2013.01); *A61B 8/14* (2013.01); *A61B 8/4281* (2013.01); *A61B 8/461* (2013.01); *A61B 8/58* (2013.01); *A61B 8/587* (2013.01)

(58) Field of Classification Search
CPC ........... A61B 8/00; A61B 8/08; A61B 8/5215; A61B 8/587
See application file for complete search history.

(56) References Cited

U.S. PATENT DOCUMENTS

| 7,995,825 B2 | 8/2011 | Jack et al. |
| 2008/0119718 A1 | 5/2008 | Hundley et al. |
| 2009/0112089 A1 | 4/2009 | Barnard et al. |

(Continued)

OTHER PUBLICATIONS

Arts, et al., Quantitative Muscle Ultrasonography in Amyotrophic Lateral Sclerosis, Ultrasound in Medicine & Biology, 2008, 34(3)354-361.

(Continued)

*Primary Examiner* — Eric D Bertram
(74) *Attorney, Agent, or Firm* — Quarles & Brady LLP

(57) ABSTRACT

Systems and methods are provided for diagnosing neuromuscular disease in a patient suspected of having a neuromuscular disease, Phantoms for use in these systems and methods are also provided. Methods are further provided for determining a normalized ultrasound data value for a patient of interest having a known age, weight, height, and sex.

23 Claims, 7 Drawing Sheets

(56) References Cited

U.S. PATENT DOCUMENTS

| | | | |
|---|---|---|---|
| 2010/0286519 A1* | 11/2010 | Lee | A61B 8/08 600/439 |
| 2011/0004099 A1 | 1/2011 | Kim | |
| 2011/0207103 A1 | 8/2011 | Trotta et al. | |
| 2013/0125963 A1 | 5/2013 | Binderbauer et al. | |
| 2013/0223714 A1 | 8/2013 | Lipton et al. | |
| 2013/0310688 A1 | 11/2013 | Rosen et al. | |
| 2017/0020491 A1* | 1/2017 | Ogawa | A61B 8/587 |

OTHER PUBLICATIONS

Boon, et al., Ultrasound-Guided Needle EMG of the Diaphragm: Technique Description and Case Report, Muscle & Nerve, 2008, 38(6):1623-1626.

Heckmatt, et al., Ultrasound Imaging in the Diagnosis of Muscle Disease, The Journal of Pediatrics, 1982, 101(5):656-660.

Heckmatt, et al., Diagnostic Advantage of Needle Muscle Biopsy and Ultrasound Imaging in the Detection of Focal Pathology in a Girl with Limb Girdle Dystrophy, Muscle & Nerve, 1985, 8(8):705-709.

Heckmatt, et al., Quantitative Sonography of Muscle, Journal of Child Neurology, 1989, 4:S101-S106.

Hellmann, et al., Diagnostic Value of Electromyography in Children and Adolescents, Journal of Clinical Neurophysiology, 2005, 22(1):43-48.

Hete, et al., A Study of the Relationship Between Mechanical and Ultrasonic Properties of Dystrophic and Normal Skeletal Muscle, Ultrasound in Medicine and Biology, 1995, 21(3):343-352.

Jones, et al., In-Vivo Characterization of Human Muscle Disease Using RF Pulse-Echo Waveforms, Ultrasound in Medicine and Biology, 1997, 23(Suppl 1):S136.

Lindequist, et al., Ultrasound Guided Needle Biopsy of Skeletal Muscle in Neuromuscular Disease, Acta Radiologica, 1990, 31(4):411-413.

Maurits, et al., Muscle Ultrasound Analysis: Normal Values and Differentiation Between Myopathies and Neuropathies, Ultrasound in Medicine and Biology, 2003, 29(2):215-225.

Maurits, et al., Muscle Ultrasound in Children: Normal Values and Application to Neuromuscular Disorders, Ultrasound in Medicine and Biology, 2004, 30(8):1017-1027.

Nielsen, et al., Quantitative Ultrasound Tissue Characterization in Shoulder and Thigh Muscles—A New Approach, BMC Musculoskeletal Disorders, 2006, 7:2, 11 pages.

Padua, et al., Contribution of Ultrasound in a Neurophysiological Lab in Diagnosing Nerve Impairment: A One-Year Systematic Assessment, Clinical Neurophysiology, 2007, 118:1410-1416.

Pillen, et al., Muscle Ultrasound in Neuromuscular Disorders, Muscle & Nerve, 2008, 37(6):679-693.

Pillen, et al., Quantitative Skeletal Muscle Ultrasonography in Children with Suspected Neuromuscular Disease, Muscle & Nerve, 2003, 27(6):699-705.

Reimers, et al., Muscular Ultrasound in Idiopathic Inflammatory Myopathies of Adults, Journal of the Neurological Sciences, 1993, 116(1):82-92.

Russell, et al., Predictive Value of Electromyography in Diagnosis and Prognosis of the Hypotonic Infant, Journal of Child Neurology, 1992, 7:387-391.

Zuberi, et al., Muscle Ultrasound in the Assessment of Suspected Neuromuscular Disease in Childhood, Neuromuscular Disorders, 1999, 9(4):203-207.

PCT International Search Report and Written Opinion, PCT/US2015/037444, dated Nov. 24, 2015.

* cited by examiner

SYSTEM AND METHOD FOR QUANTITATIVE MUSCLE ULTRASOUND FOR DIAGNOSIS OF NEUROMUSCULAR DISEASE

CROSS-REFERENCE TO RELATED APPLICATIONS

The present application represents the national stage entry of PCT International Patent Application PCT/US2015/037444 filed Jun. 24, 2015, which claims priority to U.S. Provisional Patent Application No. 62/016,945, filed Jun. 25, 2014, the entire contents of which are hereby incorporated by reference.

STATEMENT REGARDING FEDERALLY SPONSORED RESEARCH

N/A

BACKGROUND

The present disclosure relates to systems and methods for quantitative ultrasound. More particularly, the present disclosure relates to systems and methods for diagnosing neuromuscular disease in a patient suspected of having a neuromuscular disease using quantitative muscle ultrasound.

Although ultrasound has been around since the 1950s, in recent years technology has evolved to the point that portable, relatively inexpensive, high resolution machines are more widely available, leading to widespread use in almost all fields of medicine. Ultrasound provides high resolution imaging of soft tissue, fascial planes, and neurovascular structures, allowing localization of muscle, nerve, and adjacent neurovascular or other vital structures. Use of real-time ultrasound guidance for needle placement during nerve conduction studies and needle electromyography (EMG) can increase accuracy and/or decrease risk in certain situations. Ultrasound can provide detailed anatomical and pathophysiological information in nerve and muscle disease as well as real time information related to muscle activation and movement patterns of nerve and muscle. Diagnostic ultrasound has been shown to have a significant role in the diagnosis of neuromuscular disorders, for example in identifying the underlying cause of various mononeuropathies and in screening for neuromuscular disease. Neuromuscular disorders result in muscle atrophy and intramuscular fibrosis and fatty infiltration, all of which can be visualized with ultrasound. Sensitivity and specificity of muscle ultrasound in the detection of neuromuscular disorders has been shown to be very high in several prospective studies.

In the pediatric population, ultrasound is a useful tool because it is painless, rapid, and does not carry any radiation risk. Nerve conduction studies and needle EMG are typically performed under conscious sedation in pediatric patients. This exposes children to the risk of anesthesia (which is of particular concern in patients with certain neuromuscular disorders) as well as increasing the cost of the study more than five fold. The EMG study itself is often technically difficult, in many cases the child is too sedated to activate the muscles to allow for motor unit analysis and the final diagnosis may be indeterminate. Also, sensitivity of EMG in hypotonic infants and particularly in myopathy in infants and children has been shown to be quite low.

In adults, many patients with symptoms of myalgia or subjective weakness are referred to an EMG lab to rule out myopathy or other neuromuscular disease. Though representing a patient population that can tolerate the EMG process better than the pediatric population, the invasive nature is still a substantial drawback to for the adult population.

Therefore, it would be desirable to have a system method for analyzing nerves in patients without the use of needles and processes such as EMG.

SUMMARY

The present disclosure overcomes the aforementioned drawbacks by providing systems and methods for diagnosing neuromuscular disease using quantitative ultrasound, methods of determining a normalized ultrasound data values for a patient of interest, and a phantom for use with the same. Systems, methods, and phantoms described herein are suitable for diagnosing neuromuscular disease with quantitative ultrasound based on individualized, normalized data values that have been determined by observing a normalized control group and selected based on one or more patient variables.

In accordance with the present disclosure, the method of diagnosing neuromuscular disease in a patient suspected of having a neuromuscular disease using a diagnostic image processor can include receiving, at the diagnostic image processor, a patient data set comprising an ultrasound image of a muscular region of interest of the patient, the image comprising a mean signal intensity; a muscle region identifier of the muscular region of interest of the patient; a subcutaneous tissue thickness and a muscle thickness of the muscular region of interest of the patient; and at least one patient variable selected from the group consisting of an age of the patient, a weight of the patient, a height of the patient, and a sex of the patient. The method can also include determining, using the diagnostic image processor, a signal variance between the mean signal intensity and a normalized mean signal intensity and a thickness variance between the subcutaneous tissue thickness and a normalized subcutaneous tissue thickness, between the muscle thickness and a normalized muscle thickness, or between a sum of the muscle thickness and the subcutaneous tissue thickness and a sum of the normalized muscle thickness and the normalized subcutaneous tissue thickness. The method can also include categorizing, using the diagnostic image processor, the muscular region of interest based on the signal variance, the thickness variance, or a combination thereof. The normalized mean signal intensity, the normalized subcutaneous tissue thickness, and the normalized muscle thickness can be selected based on the muscle region identifier and the at least one patient variable.

In accordance with the present disclosure, a method for determining a normalized ultrasound data value for a patient of interest having a known age, weight, height, and sex includes receiving an ultrasound imaging data set comprising an ultrasound data value for each member of a normalized control group of individuals that do not have a disease state of interest. The methods further include performing a multiple linear regression on the ultrasound imaging data set based on an age of the individuals of the control group and one or more individual variables selected from the group consisting of a weight of the individuals of the control group, a height of the individuals of the control group, and a sex of the individuals of the control group to produce a multiple linear regression model. The method further includes producing, using the multiple linear regression model, a normalized ultrasound data value based on the age of the patient of interest and optionally at least one patient variable including the weight of the patient, the height of the patient, and the sex of the patient.

In accordance with the present disclosure, an ultrasound imaging phantom can include a gel and a plurality of grey scale targets within the gel. The gel can include a calibration surface, a sound velocity ranging from about 1400 m/s to about 1700 m/s, and a sound absorption ranging from about 0.3 dB/cm/MHz to about 1.0 dB/cm/MHz. The plurality of grey scale targets can include a first grey scale target and a second grey scale target. The first grey scale target can have a mean echo intensity of at least about +18 dB and is located at a first depth from the calibration surface. The second grey scale target can have a mean echo intensity equal to the first grey scale target and can be located at a second depth from the calibration surface. The second depth can be different than the first depth. The first and second grey scale targets can each have at least one physical dimension ranging from about 0.1 mm to about 5.0 mm. The first and second depths can be from about 0.1 cm to about 10.0 cm.

In accordance with the present disclosure, an ultrasound diagnostic system can include an ultrasound imaging system; a phantom; and a diagnostic image processor.

The foregoing and other aspects and advantages of the disclosure will appear from the following description. In the description, reference is made to the accompanying drawings that form a part hereof, and in which there is shown by way of illustration a preferred aspect of the disclosure. Such aspect does not necessarily represent the full scope of the disclosure, however, and reference is made therefore to the claims and herein for interpreting the scope of the disclosure.

DETAILED DESCRIPTION

The present disclosure is not limited to the particular embodiments described. It is also to be understood that the terminology used herein is for the purpose of describing particular embodiments only, and is not intended to be limiting. The scope of the present disclosure will be limited only by the claims. As used herein, the singular forms "a", "an", and "the" include plural embodiments unless the context clearly dictates otherwise.

Specific structures, devices, and methods relating to improved ultrasound treatment efficiency and operation are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value ranging from 1 to 10 or from 2 to 9 also contemplates a value ranging from 1 to 9 or from 2 to 10. Ranges identified as being "ranging from" two values are inclusive of the end-point values. For example, recitation of a value ranging from 1 to 10 includes the values 1 and 10.

This disclosure provides ultrasound diagnostic systems. The ultrasound diagnostic systems may include one or more of the following: an ultrasound imaging system; a phantom; and a diagnostic image processor.

Figure 1A:
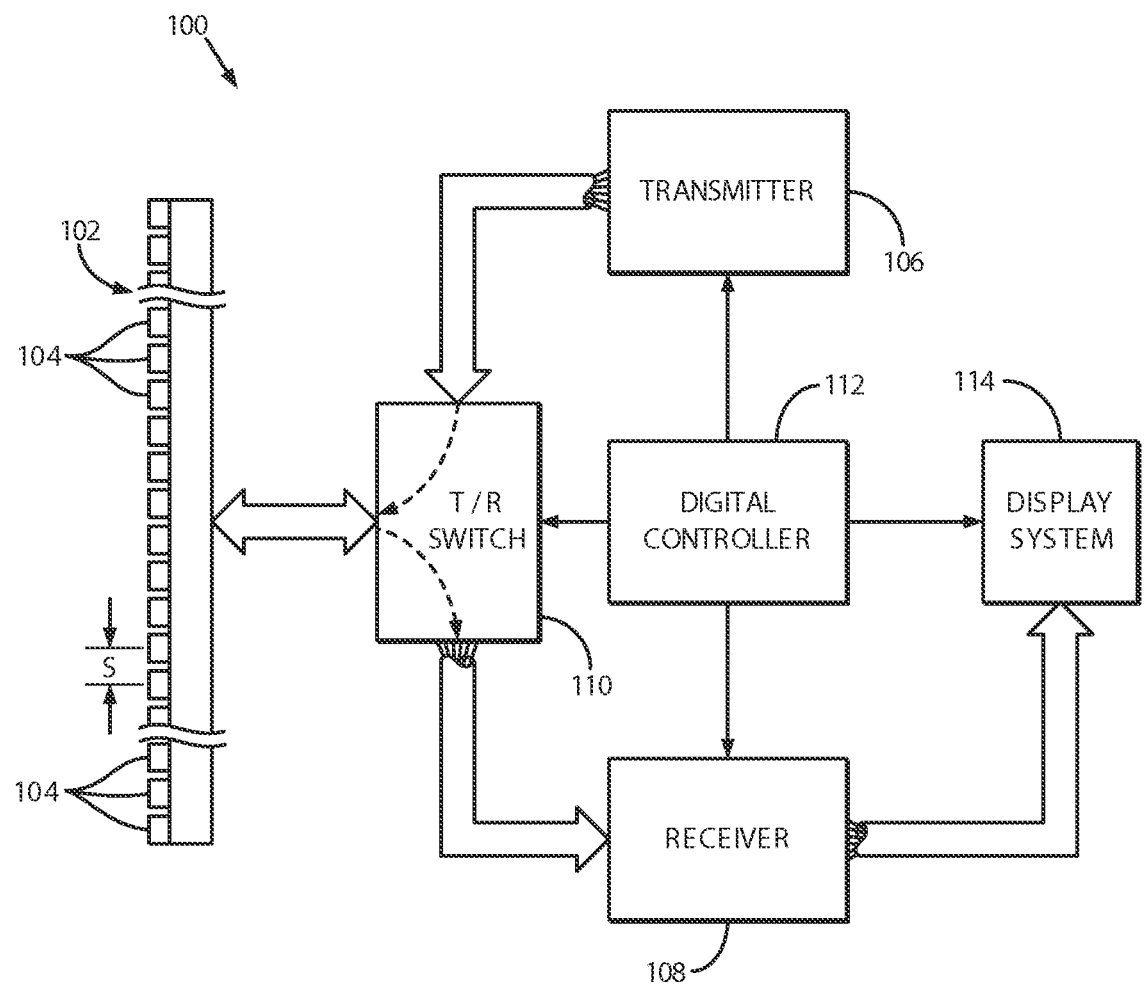
FIG. 1A is a schematic of an ultrasound imaging system, in accordance with the present disclosure.

Referring particularly to FIG. 1A, an example of an ultrasound imaging system 100 includes a transducer array 102 that includes a plurality of separately driven transducer elements 104. In some configurations, the transducer array 102 may include a linear array transducer.

When energized by a transmitter 106, each transducer element 104 produces a burst of ultrasonic energy. The ultrasonic energy reflected back to the transducer array 102 from the object or subject under study is converted to an electrical signal by each transducer element 104 and applied separately to a receiver 108 through a set of switches 110. The transmitter 106, receiver 108, and switches 110 are operated under the control of a digital controller 112 responsive to commands input by a user. A complete scan is performed by acquiring a series of echo signals in which the switches 110 are set to their transmit position, thereby directing the transmitter 106 to be turned on momentarily to energize each transducer element 104. The switches 110 are then set to their receive position and the subsequent echo signals produced by each transducer element 104 are measured and applied to the receiver 108. The separate echo signals from each transducer element 104 are combined in the receiver 108 to produce a single echo signal that is employed to produce a line in an image, for example, on a display system 114.

The present disclosure recognizes that quantitative ultrasound imaging using a system such as described with respect to FIG. 1A offers the ability to track changes in muscular composition non-invasively. This disclosure provides systems and methods for diagnosing neuromuscular disease in a patient suspected of having a neuromuscular disease. The methods may include one or more of the following: receiving a patient data set; determining a signal variance and a thickness variance; and categorizing the muscular region of interest.

Figure 1B:
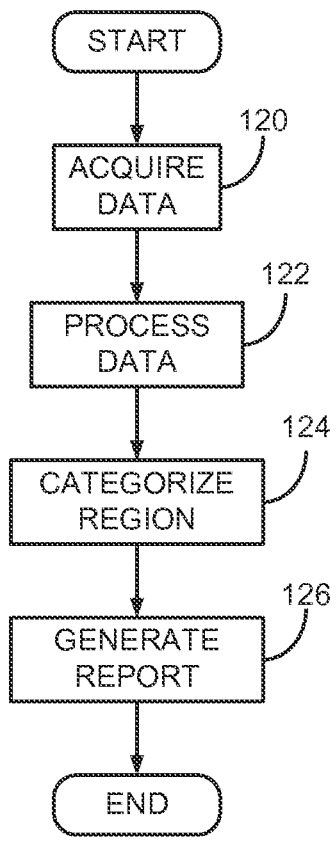
FIG. 1B is a flow chart setting forth steps of an example of a method, in accordance with the present disclosure.

In particular, referring to FIG. 1B, a flow chart is provided setting forth examples of steps of a method that may be performed in accordance with the present disclosure for performing quantitative ultrasound imaging and tracking such information over time to make informed clinical decisions. Specifically, at process block 120, an ultrasound system, such as described with respect to FIG. 1A, is used to acquire quantitative ultrasound data forming a patient data set. In certain configurations, the patient data set may include ultrasound images of a muscular region of interest of the patient and/or a muscle region identifier of the muscular region of interest of the patient.

The ultrasound image of a muscular region of interest of the patient may include a mean signal intensity. In certain configurations, the mean signal intensity may be determined using the histogram method, such as the method described in U.S. Patent Application Pub. No. 2008/0119718 and U.S. Pat. No. 7,995,825, each of which is incorporated herein in its entirety by reference. In certain configurations, the mean signal intensity may be determined using software. In certain configurations, the mean signal intensity may be determined using two, three, four, five, six, seven, eight, nine, ten, or more individual ultrasound images.

The muscle region identifier may be used to identify the muscle or the sub-region of a muscle that is the subject of the ultrasound image. The muscle region identifier can take a variety of forms and can be used to identify the muscle or sub-region of the muscle. For example, the muscle region identifier can be a word, such as the name of the muscle or sub-region of the muscle, a numerical value that corresponds to the name of the muscle or sub-region of the muscle, or the like.

At process block 122, the acquired ultrasound data may be processed. For example, the data may be processed to determine a subcutaneous thickness of the muscular region of interest of the patient and/or determine a muscle thickness of the muscular region of interest of the patient and/or evaluate one or more patient variables.

The subcutaneous thickness is a value that corresponds to the thickness of the subcutaneous tissue that is adjacent to and in contact with the muscle that contains the muscular region of interest. The subcutaneous thickness can be measured by a method known to those having ordinary skill in the art. For example, the subcutaneous thickness can be measured by caliper, ultrasound imaging, magnetic resonance imaging, or the like. For improved reproducibility, the subcutaneous thickness may be measured by a technique that produces results that are comparable with the technique used to measure the subcutaneous thicknesses that are used to determine a normalized subcutaneous thickness.

The muscle thickness is a value that corresponds to the thickness of the muscle that contains the muscular region of interest. The muscle thickness can be measured by a method known to those having ordinary skill in the art. For example, the muscle thickness can be measured by caliper, ultrasound imaging, magnetic resonance imaging, or the like. For improved reproducibility, the muscle thickness may be measured by a technique that produces results that are comparable with the technique used to measure the muscle thicknesses that are used to determine a normalized muscle thickness.

The one or more patient variables are used to determine which normalized values may be used for determining a signal and thickness variance, as described below. The one or more patient variables include, but are not limited to, age, height, weight, and sex. In some configurations, the one or more patient variables include age and one or more of height, weight, and sex.

In certain configurations, determining a signal variance may include determining a variance between the mean signal intensity and a normalized mean signal intensity. The signal variance may be determined by a method known to a person having ordinary skill in the art. For example, the signal variance can be determined by calculating the difference between the mean signal intensity and the normalized mean signal intensity.

In certain configurations, determining a thickness variance may include determining a variance between the subcutaneous tissue thickness and a normalized subcutaneous tissue thickness, between the muscle thickness and a normalized muscle thickness, or between a sum of the muscle thickness and the subcutaneous tissue thickness and a sum of the normalized muscle thickness and the normalized subcutaneous tissue thickness. The thickness variance may be determined by a method known to a person having ordinary skill in the art. For example, the thickness variance can be determined by calculating the difference between the subcutaneous tissue thickness and a normalized subcutaneous tissue thickness, between the muscle thickness and the normalized muscle thickness, or between a sum of the muscle thickness and the subcutaneous tissue thickness and a sum of the normalized muscle thickness and the normalized subcutaneous tissue thickness.

At process block 124, the muscular region of interest is categorized. Categorizing the muscular region of interest is a step that converts the data into a more informative form for consumption by a medical professional. Rather than reporting a numerical value of questionable use to a medical professional, the methods described herein can categorize the muscular region of interest based on one or more of the numerical outputs described herein. In certain configurations, categorizing the muscular region of interest may include categorizing the muscular region of interest based on the signal variance, the thickness variance, or a combination thereof Categorizing the muscular region of interest may include establishing one or more cut-off points. A cut-off point may be a point that denotes a shift between categories. For example, a first category and a second category may be divided at a cut-off point with the first category residing below the cut-off point and the second category residing above the cut-off point. If a data value is above the cut-off point, then the muscular region of interest is categorized in the second category. If a data value is below the cut-off point, then the muscular region of interest is categorized in the first category. A cut-off point can be included in either the category residing above or below the cut-off point. In some configurations, the one or more cut-off points establish categories of diagnostic relevance. In certain configurations, the cut-off point for a data value may be ±2 standard deviations from the normalized data value. However, a person of ordinary skill in the art will recognize that the cut-off point can be adjusted as desired based, for example, on desired or desired numbers of categories. Categorizing the muscular region of interest can include categorizing into categories such as normal, abnormal, borderline abnormal, and the like.

At process block 126, a report may be generated. For example, the report may include the categorized muscular region of interest.

The normalized mean signal intensity, the normalized subcutaneous tissue thickness, or the normalized muscle thickness may be calculated or selected based on the muscle region identifier and at least one patient variable. For example, a quadriceps muscle for a 10 year old male may have a different normalized mean signal intensity, normalized subcutaneous tissue thickness, or normalized muscle thickness than a quadriceps muscle for a 70 year old female.

Figure 1C:
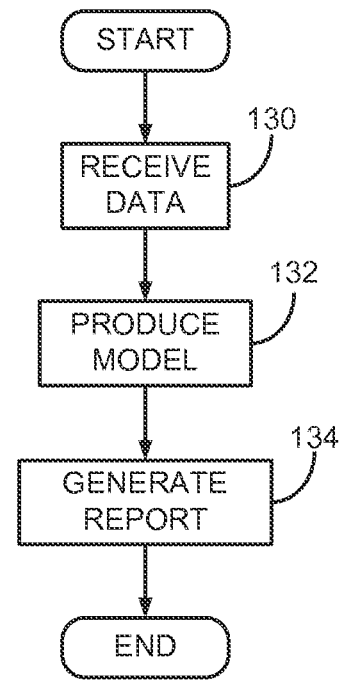
FIG. 1C is a flow chart setting forth steps of an example of a method in accordance with the present disclosure.

Referring to FIG. 1C, the above-described information may be used to determine a normalized ultrasound data value for a patient of interest having a known age, weight, height, and sex. As will be described in greater detail, one example of one method may include receiving an ultrasound imaging data set at process block 130, performing a multiple linear regression on the ultrasound imaging data set to produce a multiple linear regression model at process block 132, and producing a report at process block 134, using the multiple linear regression model. The report may include a normalized ultrasound data value based on one or more patient variables.

The ultrasound data value and normalized ultrasound data value may be related to particular muscles or particular sub-regions of muscles. In other words, an ultrasound data value and normalized ultrasound data value for a quadriceps muscle may be different than an ultrasound data value and normalized ultrasound data value for a biceps muscle. It should be apparent to a person having ordinary skill in the art that this method affords the inclusion of a muscle region of interest as one of the regression variables, but the method described in detail herein is related to a single muscle or sub-region of a muscle. In other words, the methods described herein can be performed on a muscle-by-muscle or sub-region-by-sub-region basis, or can be combined into a larger method that deals with more than one muscle or sub-region of muscle at the same time.

In certain configurations, the ultrasound imaging data set may include an ultrasound data value for each member of a normalized control group of healthy individuals or individuals that do not have a disease state of interest. The ultrasound data value and the ultrasound imaging data set may be created using the histogram method. In certain configurations, the ultrasound data value may include a mean echo intensity, a subcutaneous tissue thickness, a muscle thickness, or a combination thereof. In certain configurations, performing a multiple linear regression on the ultrasound imaging data set may include a regression method known to those having ordinary skill in the art. In certain configurations, the multiple linear regression may be based on an age of the individuals of the control group, a weight of the individuals of the control group, a height of the individuals of the control group, and a sex of the individuals of the control group. Performing the multiple linear regression produces a multiple linear regression model.

In certain configurations, producing a normalized ultrasound data value may include producing, using the multiple linear regression model, a normalized ultrasound data value based on one or more patient variables. In some configurations, producing a normalized ultrasound data value may include producing, using the multiple linear regression model, a normalized ultrasound data value based on an age of the patient and at least one patient variable including a weight of the patient, a height of the patient, and a sex of the patient. In certain configurations, producing a normalized ultrasound data value may comprise inputting one or more patient variables into the multiple linear regression model.

A normalized control group of healthy individuals or individuals that do not have a disease state of interest is a group that is representative of one or more of the patient variables as described herein. In certain configurations, a normalized control group of healthy individuals or individuals that do not have a disease state of interest comprises at least five individuals for each age year for ages 18 and below, at least 20 individuals for each decade for ages above 18, or a combination thereof. In certain configurations, the methods and systems described herein are suitable for persons aged 0 to 100, persons ages 0 to 18, persons aged 19 to 100, or a subset or combination thereof.

Figure 2:
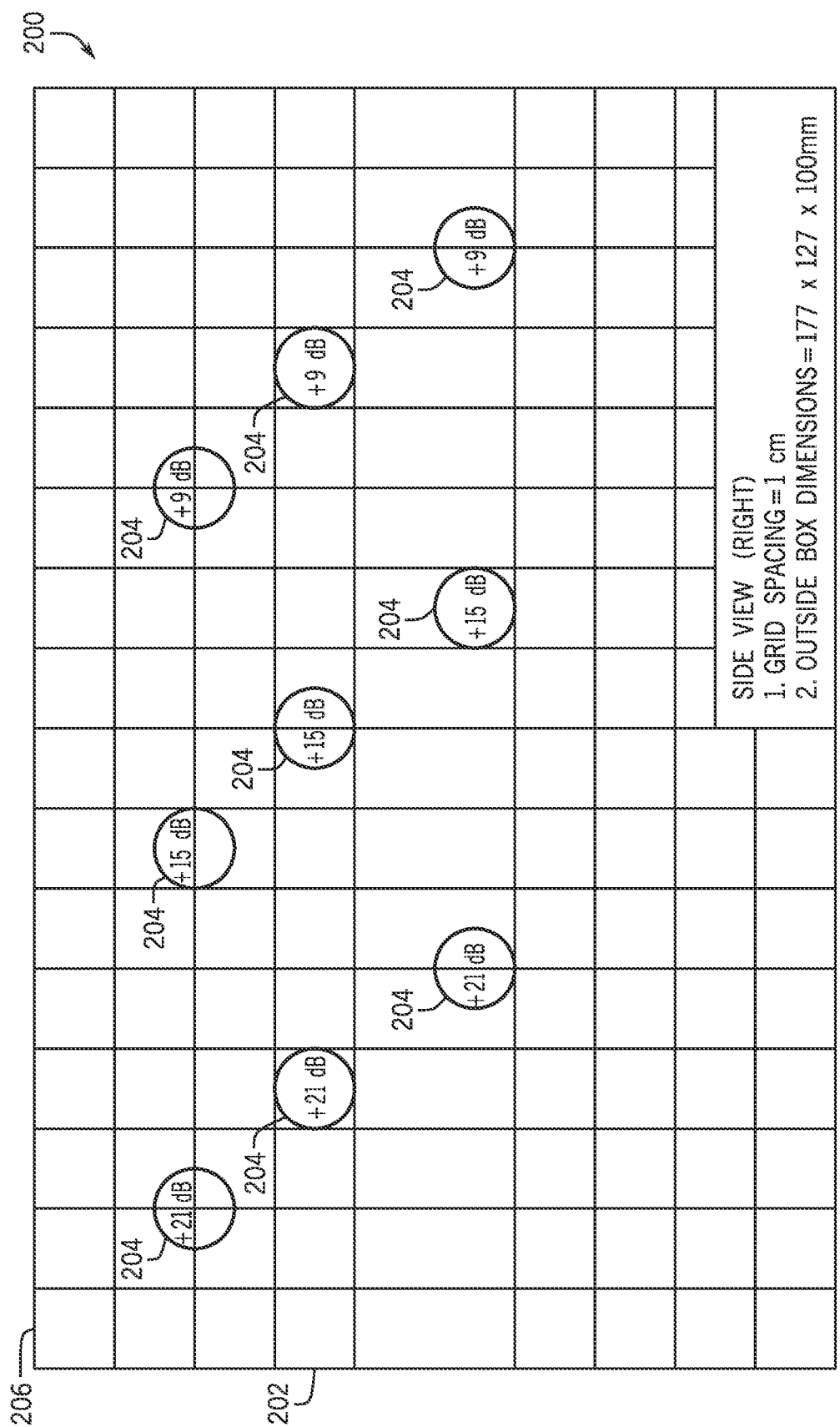
FIG. 2 is a schematic side view (first side) of a phantom, in accordance with the present disclosure.
Figure 3:
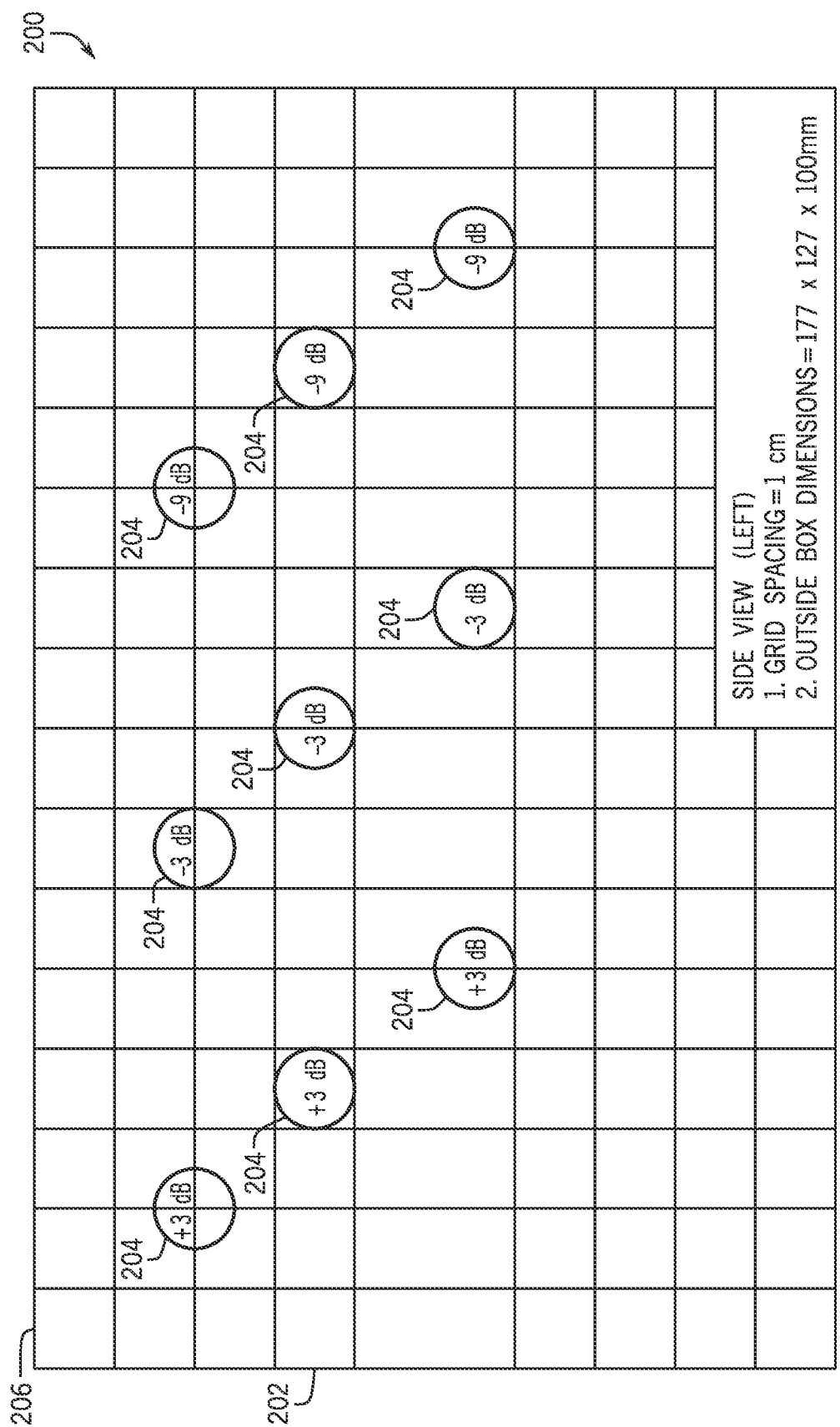
FIG. 3 is a schematic side view (opposite side of FIG. 2) of a phantom, in accordance with the present disclosure.
Figure 4:
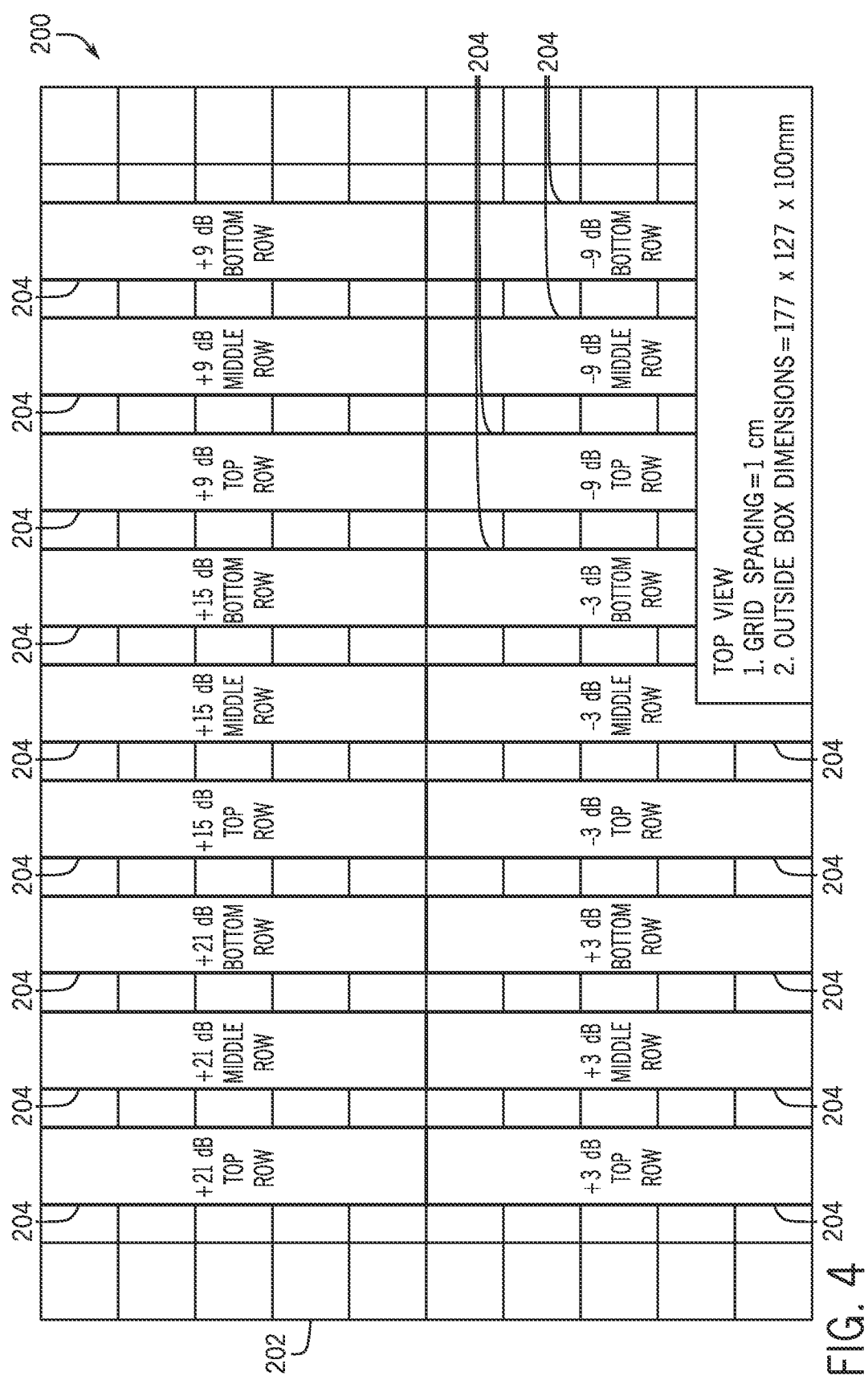
FIG. 4 is a schematic top view of a phantom, in accordance with the present disclosure.

This disclosure also provides ultrasound imaging phantoms. Referring to FIGS. 2-4, a phantom 200 may include a gel 202 and a plurality of grey scale targets 204 within the gel 202. In certain configurations, the gel 202 may include a material with material properties that are similar to healthy muscle tissue. In certain configurations, the gel 202 may include a tissue-mimicking hydrogel. In certain configurations, the gel 202 may include a Zerdine® tissue-mimicking hydrogel (available commercially from CIRS, Inc., Norfolk, Va.). In certain configurations, the get 202 may include a calibration surface 206, which in some aspects is a top surface 206. The calibration or top surface 206 is the surface from which an ultrasound calibration may be performed. The calibration or top surface 206 is the surface from which the depths of the plurality of grey scale targets 204 are defined. In certain configurations, the gel 202 may include a sound velocity ranging from about 1400 m/s to about 1700 m/s, including but not limited to, a sound velocity ranging from about 1450 m/s to 1650 m/s, from about 1500 m/s to about 1600 m/s, or from about 1525 m/s to about 1575 m/s. In some configurations, the gel 202 may include a sound velocity of about 1540 m/s. In certain configurations, the gel 202 may include a sound absorption ranging from about 0.3 dB/cm/MHz to about 1.0 dB/cm/MHz, including but not limited to, a sound absorption ranging from about 0.35 dB/cm/MHz to about 0.8 dB/cm/MHz, from about 0.4 dB/cm/MHz to about 0.6 dB/cm/MHz, or from about 0.45 dB/cm/MHz to about 0.55 dB/cm/MHz. In some configurations, the gel 202 may include a sound absorption of about 0.5 dB/cm/MHz.

In certain configurations, the plurality of grey scale targets 204 may include two or more grey scale targets 204 with properties that are suitable for calibrating an ultrasound imaging system as described herein to perform the methods as described herein. In certain configurations, each of the plurality of grey scale targets 204 is located at a depth below the calibration surface 206 and positioned beneath a location on the calibration surface 206. In preferred configurations, the phantom 200 includes one grey scale target beneath a given location, such that an ultrasound measurement above a given target can be identified as pertaining to said target.

The plurality of grey scale targets 204 may include sets of targets, wherein each of the targets within a set of targets produces about the same mean echo intensity, in certain configurations, a set of targets may include two, three, four, five, six, seven, eight, nine, ten, or more targets, each producing about the same mean echo intensity. Each member of a set of targets may be located at a different depth than the other members of the set of targets. This feature can be useful for depth-specific calibration.

The grey values of the targets should encompass the full grey scale range of normalized mean echo intensities as described herein. In addition, the grey values of the targets should encompass the pathologically increased echo intensities relating to non-normal muscle tissue, such as diseased muscle tissue.

In order to achieve higher echo intensities, a grey scale target that is larger than those typically used may be employed. In certain configurations, one or more of the plurality of grey scale targets 204 may include at least one physical dimension ranging from about 0.1 mm to about 5.0 mm, in some configurations, one or more of the plurality of grey scale targets 204 may include at least one physical dimension ranging from about 0.5 mm to about 2.0 mm, including but not limited to at least one physical dimension ranging from about 0.75 mm to about 1.5 mm, or from about 0.9 mm to about 1.25 mm. In certain configurations, one or more of the plurality of grey scale targets 204 may include a mean echo intensity of at least about +18 dB.

In certain configurations, each of the plurality of grey scale targets 204 is located at a depth from the calibration or top surface 206 of the gel 202 ranging from about 0.1 cm to about 10.0 cm. In certain configurations, each of the plurality of grey scale targets 204 is located at a depth from the calibration or top surface 206 of the gel 202 ranging from about 0.5 cm to about 6.0 cm.

As shown in FIGS. 2-4, the plurality of grey scale targets 204 may include the following: a set of three −9 dB targets, one at a first depth, one at a second depth, and one at a third depth; a set of three −3 dB targets, one at a first depth, one at a second depth, and one at a third depth; a set of three +3 dB targets, one at a first depth, one at a second depth, and one at a third depth; a set of three +9 dB targets, one at a first depth, one at a second depth, and one at a third depth; a set of three +15 dB targets, one at a first depth, one at a second depth, and one at a third depth; and a set of three +21 dB targets, one at a first depth, one at a second depth, and one at a third depth. The particular depths and spatial configuration shown in FIGS. 2-4 can be altered in numerous ways as would be apparent to a person having ordinary skill in the art.

Figure 5:
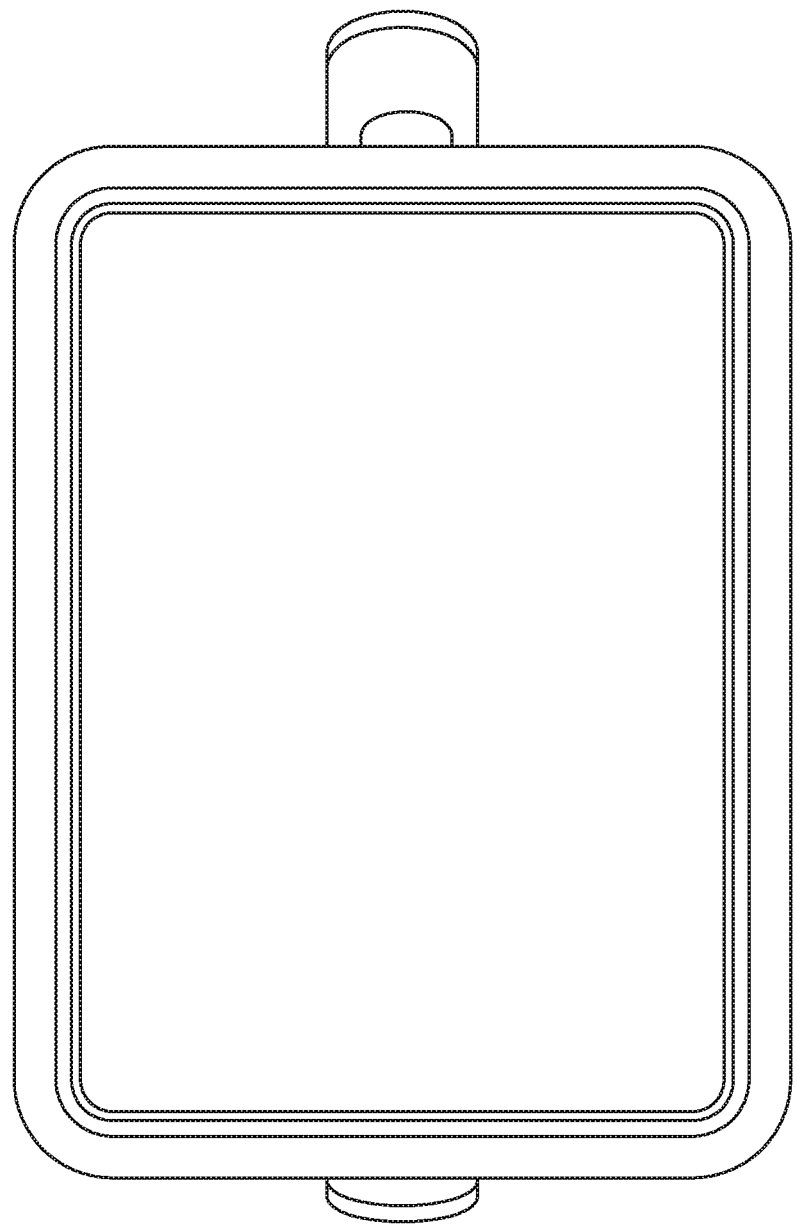
FIG. 5 is an optical image of a top view of a phantom, in accordance with the present disclosure.
Figure 6:
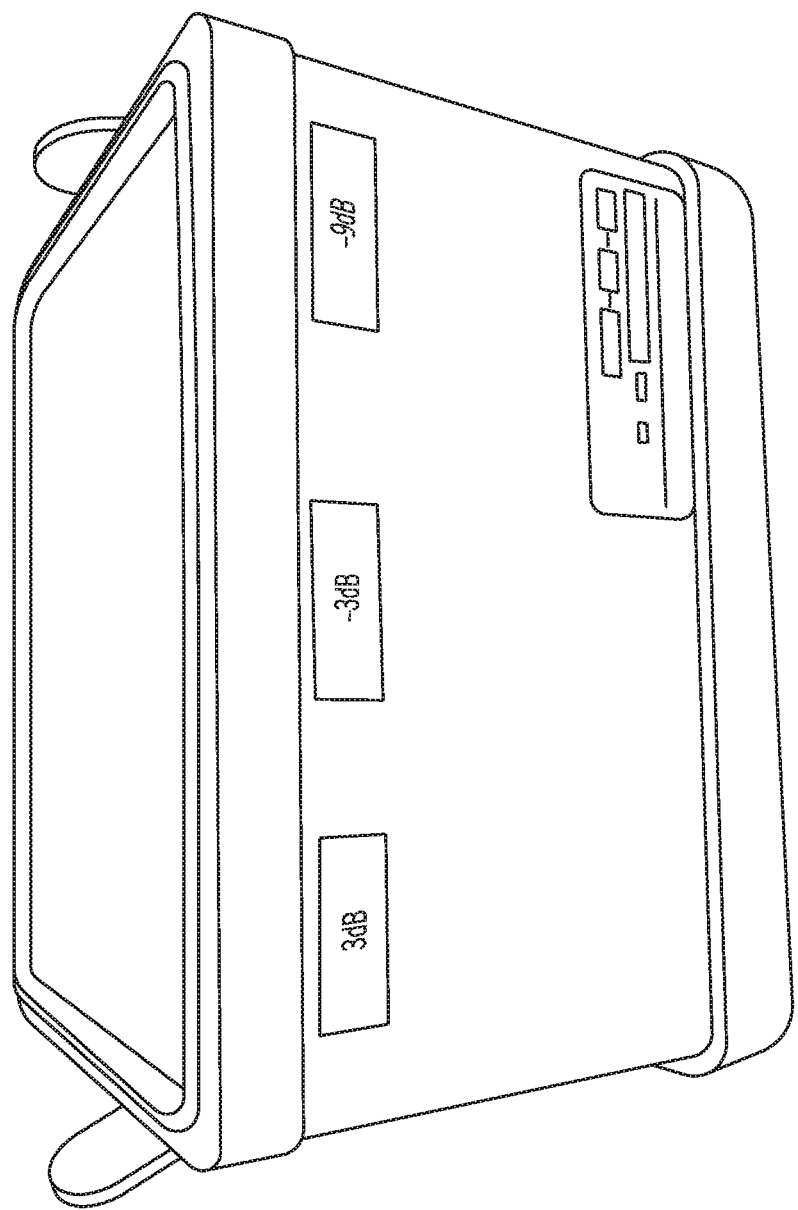
FIG. 6 is an optical image of a side view of a phantom, in accordance with the present disclosure.

In one particular configuration, the phantom 200 may be a durable, easily transportable, phantom 200 with a series of cylindrical greyscale targets 204 on calibrated backscatter contrast levels ranging from −9 dB to +21 dB with respect to the background. The phantom 200 contains three rows of targets 204 at different depths (1, 3 and 5 cm) to allow users to make depth-dependent corrections of the contrast level. The phantom 200 may be constructed of CIRS, Inc.'s, Zerdine® tissue-mimicking hydrogel and is housed in a rugged ABS plastic for increased durability. FIGS. 5-6 show optical images of one example of a phantom 200 according to the present disclosure. In certain configurations, the phantom 200 may be easily transportable, durable, and environmentally stable.

Thus, system hardware and methods are provided such that: variability in echointensities from one system to the next is controlled, which has been the limiting factor with prior efforts. The above-described hardware can keep all the settings unchanged from one exam to another.

The present disclosure has been described in terms of one or more preferred aspects, and it should be appreciated that many equivalents, alternatives, variations, and modifications, aside from those expressly stated, are possible and within the scope of the disclosure.

I claim:

1. An ultrasound diagnostic system comprising an ultrasound imaging system, an ultrasound imaging phantom, and a diagnostic image processor,
the ultrasound imaging system configured to acquire an ultrasound image of a muscular region of interest of a patient and transmit the ultrasound image to the diagnostic image processor, the ultrasound image comprising a mean signal intensity;
the diagnostic image processor configured to:
receive a patient data set comprising:
the ultrasound image of the muscular region of interest of the patient;
a muscle region identifier of the muscular region of interest of the patient;
a subcutaneous tissue thickness and a muscle thickness of the muscular region of interest of the patient; and
at least one patient variable selected from the group consisting of an age of the patient, a weight of the patient, a height of the patient, and a sex of the patient;
determine a signal variance between the mean signal intensity and a normalized mean signal intensity and a thickness variance between the subcutaneous tissue thickness and a normalized subcutaneous tissue thickness, between the muscle thickness and a normalized muscle thickness, or between a sum of the muscle thickness and the subcutaneous tissue thickness and a sum of the normalized muscle thickness and the normalized subcutaneous tissue thickness;
categorize the muscular region of interest based on the signal variance, the thickness variance, or a combination thereof, wherein the normalized mean signal intensity, the normalized subcutaneous tissue thickness, and the normalized muscle thickness are selected based on the muscle region identifier and the one or more patient variables;
the ultrasound phantom comprising:
a gel having a calibration surface; and
a plurality of grey scale targets within the gel,
wherein a first grey scale target has a first mean echo intensity and is located at a first depth from the calibration surface, and
wherein a second grey scale target has a second mean echo intensity equal to the first mean echo intensity and is located at a second depth from the calibration surface, wherein the second depth is different than the first depth.

2. The system of claim 1, wherein the muscle region identifier is a word or a number representing the muscular region of interest.

3. The system of claim 1, wherein the subcutaneous tissue thickness or the muscle thickness of the muscular region of interest of the patient is measured by the ultrasound imaging system.

4. The system of claim 1, wherein the at least one patient variable is at least two patient variables.

5. The system of claim 4, wherein the at least two patient variables include the age of the patient and the weight of the patient, the height of the patient, or the sex of the patient.

6. The system of claim 1, wherein the at least one patient variable is at least four patient variables, the at least four patient variables including the age of the patient, the weight of the patient, the height of the patient, and the sex of the patient.

7. The system of claim 1, wherein the normalized mean signal intensity, the normalized subcutaneous thickness, or the normalized muscle thickness is calculated based on the muscle region identifier and the at least one patient variable.

8. The system of claim 1, wherein the normalized mean signal intensity, the normalized subcutaneous thickness, or the normalized muscle thickness is calculated using a multiple linear regression model generated from data collected from a normalized control group of individuals that do not have a disease state of healthy individuals.

9. The system of claim 1, wherein the diagnostic image processor is configured to categorize the muscular region of interest into at least a normal category and an abnormal category.

10. The system of claim 1, wherein the gel has a sound velocity ranging from about 1400 m/s to about 1700 m/s.

11. The system of claim 1, wherein the gel has a sound absorption ranging from about 0.3 dB/cm/MHz to about 1.0 dB/cm/MHz.

12. The system of claim 1, wherein the first mean echo intensity is at least about +18 dB.

13. The system of claim 1, wherein the first and second grey scale targets each have at least one physical dimension ranging from about 0.1 mm to about 5.0 mm.

14. The system of claim 1, wherein the first and second depth are from about 0.1 cm to about 10.0 cm.

15. A method of diagnosing neuromuscular disease in a patient suspected of having a neuromuscular disease using a diagnostic image processor, the method comprising:
   receiving, at the diagnostic image processor, a patient data set comprising:
      an ultrasound image of a muscular region of interest of the patient, the ultrasound image comprising a mean signal intensity;
      a muscle region identifier of the muscular region of interest of the patient;
      a subcutaneous tissue thickness and a muscle thickness of the muscular region of interest of the patient; and
      at least one patient variable selected from the group consisting of an age of the patient, a weight of the patient, a height of the patient, and a sex of the patient;
   determining, using the diagnostic image processor, a signal variance between the mean signal intensity and a normalized mean signal intensity and a thickness variance between the subcutaneous tissue thickness and a normalized subcutaneous tissue thickness, between the muscle thickness and a normalized muscle thickness, or between a sum of the muscle thickness and the subcutaneous tissue thickness and a sum of the normalized muscle thickness and the normalized subcutaneous tissue thickness; and
   categorizing, using the diagnostic image processor, the muscular region of interest based on the signal variance, the thickness variance, or a combination thereof,
   wherein the normalized mean signal intensity, the normalized subcutaneous tissue thickness, and the normalized muscle thickness are selected based on the muscle region identifier and the at least one patient variable.

16. The method of claim 15, wherein the muscle region identifier is a word or a number representing the muscular region of interest.

17. The method of claim 15, wherein the at least one patient variable is at least two patient variables.

18. The method of claim 17, wherein the at least two patient variable include the age of the patient and the weight of the patient, the height of the patient, or the sex of the patient.

19. The method of claim 15, wherein the at least one patient variable is at least four patient variables, the at least four patient variables including the age of the patient, the weight of the patient, the height of the patient, and the sex of the patient.

20. The method of claim 15, wherein a first and second grey scale targets each have at least one physical dimension ranging from about 0.1 mm to about 5.0 mm.

21. The method of claim 15, wherein the normalized mean signal intensity, the normalized subcutaneous thickness, or the normalized muscle thickness is calculated using a multiple linear regression model generated from data collected from a normalized control group of individuals that do not have a disease state of healthy individuals.

22. The method of claim 15, wherein categorizing the muscular region of interest includes categorizing the muscular region of interest into at least a normal category and an abnormal category.

23. An ultrasound imaging phantom comprising:
   a gel having a calibration surface, the gel comprising a sound velocity ranging from about 1400 m/s to about 1700 m/s and a sound absorption ranging from about 0.3 dB/cm/MHz to about 1.0 dB/cm/MHz; and
   a plurality of grey scale targets within the gel,
   wherein a first grey scale target has a mean echo intensity of at least about +18 dB and is located at a first depth from the calibration surface,
   wherein a second grey scale target has a mean echo intensity equal to the first grey scale target and is located at a second depth from the calibration surface, wherein the second depth is different than the first depth,
   wherein the first and second grey scale targets each have at least one physical dimension ranging from about 0.1 mm to about 5.0 mm, and
   wherein the first and second depths are from about 0.1 cm to about 10.0 cm.

* * * * *